(12) United States Patent
Fridman et al.

(10) Patent No.: US 8,295,937 B2
(45) Date of Patent: Oct. 23, 2012

(54) OPTIMIZING PITCH ALLOCATION IN A COCHLEAR STIMULATION SYSTEM

(75) Inventors: Gene Y. Fridman, Santa Clarita, CA (US); Leonid M. Litvak, Los Angeles, CA (US)

(73) Assignee: Advanced Bionics, LLC, Valencia, CA (US)

(*) Notice: Subject to any disclaimer, the term of this patent is extended or adjusted under 35 U.S.C. 154(b) by 0 days.

(21) Appl. No.: 13/225,981

(22) Filed: Sep. 6, 2011

(65) Prior Publication Data
US 2011/0319965 A1 Dec. 29, 2011

Related U.S. Application Data

(63) Continuation of application No. 11/262,055, filed on Oct. 28, 2005, now Pat. No. 8,027,733.

(51) Int. Cl.
*A61N 1/00* (2006.01)
*A61B 5/04* (2006.01)

(52) U.S. Cl. ............... 607/57; 607/50; 607/55; 600/372

(58) Field of Classification Search .............. 607/50, 607/55, 57; 600/372
See application file for complete search history.

(56) References Cited

U.S. PATENT DOCUMENTS

| | | | |
|---|---|---|---|
| 3,751,605 A | 8/1973 | Michelson | |
| 4,284,856 A | 8/1981 | Hochmair et al. | |
| 4,400,590 A | 8/1983 | Michelson | |
| 4,495,384 A | 1/1985 | Scott et al. | |
| 4,793,353 A | 12/1988 | Borkan | |
| 4,819,647 A | 4/1989 | Byers et al. | |
| 5,069,210 A | 12/1991 | Jeutter et al. | |
| 5,603,726 A | 2/1997 | Schulman et al. | |
| 5,626,629 A | 5/1997 | Faltys et al. | |
| 5,776,172 A | 7/1998 | Schulman et al. | |
| 5,876,443 A | 3/1999 | Hochmair et al. | |
| 5,938,691 A | 8/1999 | Schulman et al. | |
| 6,052,624 A | 4/2000 | Mann | |

(Continued)

FOREIGN PATENT DOCUMENTS

WO 00/01200 1/2000

(Continued)

OTHER PUBLICATIONS

U.S. Appl. No. 60/383,157, filed May 23, 2002, Ayal.

(Continued)

*Primary Examiner* — Niketa Patel
*Assistant Examiner* — Nicole F Lavert
(74) *Attorney, Agent, or Firm* — Wong, Cabello, Lutsch, Rutherford, & Brucculeri, LLP

(57) ABSTRACT

Optimizing pitch allocation in a cochlear stimulation system may include implanting an electrode array having a plurality of electrodes into the cochlea of a patient, where the electrode array has an associated implant fitting characteristic that defines a relationship between the implanted electrode array and audio frequencies, presenting sounds through the electrode array to the patient, receiving from the patient a selection of one of the sounds that most closely conforms to a single note, and determining a slope of the implant fitting characteristic of the electrode array based on the sound selected by the patient. Each sound may include a fundamental frequency and one or more harmonics. The optimization may also include changing a center frequency of a band pass filter associated with each electrode based on the determined slope.

40 Claims, 10 Drawing Sheets

U.S. PATENT DOCUMENTS

| | | | |
|---|---|---|---|
| 6,067,474 A | 5/2000 | Schulman et al. | |
| 6,078,838 A | 6/2000 | Rubinstein | |
| 6,129,753 A | 10/2000 | Kuzma | |
| 6,154,678 A | 11/2000 | Lauro | |
| 6,157,861 A | 12/2000 | Faltys et al. | |
| 6,181,969 B1 | 1/2001 | Gord | |
| 6,195,585 B1 | 2/2001 | Karunasiri et al. | |
| 6,205,360 B1 | 3/2001 | Carter et al. | |
| 6,208,882 B1 | 3/2001 | Lenarz et al. | |
| 6,214,046 B1 | 4/2001 | Kennedy | |
| 6,216,040 B1 | 4/2001 | Harrison | |
| 6,216,045 B1 | 4/2001 | Black et al. | |
| 6,219,580 B1 | 4/2001 | Faltys et al. | |
| 6,249,704 B1 | 6/2001 | Maltan et al. | |
| 6,272,382 B1 | 8/2001 | Faltys et al. | |
| 6,289,247 B1 | 9/2001 | Faltys et al. | |
| 6,295,467 B1 | 9/2001 | Kollmeier et al. | |
| 6,390,971 B1 | 5/2002 | Adams et al. | |
| 6,393,325 B1 | 5/2002 | Mann et al. | |
| 6,414,229 B1 * | 7/2002 | Gaudet | 84/465 |
| 6,415,185 B1 | 7/2002 | Maltan | |
| 6,516,227 B1 | 2/2003 | Meadows et al. | |
| 6,572,531 B2 | 6/2003 | Zilberman et al. | |
| 6,604,283 B1 | 8/2003 | Kuzma | |
| 6,694,035 B1 * | 2/2004 | Teicher et al. | 381/326 |
| 6,728,578 B1 | 4/2004 | Voelkel | |
| 6,732,073 B1 | 5/2004 | Kluender et al. | |
| 6,915,166 B1 | 7/2005 | Stecker et al. | |
| 6,925,332 B2 | 8/2005 | Franck | |
| 7,054,689 B1 | 5/2006 | Whitehurst et al. | |
| 7,200,504 B1 | 4/2007 | Fister | |
| 7,203,548 B2 | 4/2007 | Whitehurst et al. | |
| 7,242,985 B1 | 7/2007 | Fridman et al. | |
| 7,251,530 B1 | 7/2007 | Overstreet et al. | |
| 7,277,760 B1 | 10/2007 | Litvak et al. | |
| 7,292,890 B2 | 11/2007 | Whitehurst et al. | |
| 7,292,891 B2 | 11/2007 | Hartley et al. | |
| 7,292,892 B2 * | 11/2007 | Litvak et al. | 607/57 |
| 7,308,303 B2 | 12/2007 | Whitehurst et al. | |
| 7,317,945 B2 | 1/2008 | Litvak et al. | |
| 7,450,994 B1 | 11/2008 | Mishra et al. | |
| 7,522,961 B2 | 4/2009 | Fridman et al. | |
| 7,599,500 B1 | 10/2009 | Segel et al. | |
| 7,627,379 B2 | 12/2009 | Kitazawa et al. | |
| 7,660,633 B2 | 2/2010 | Darley et al. | |
| 7,702,396 B2 | 4/2010 | Litvak et al. | |
| 7,729,758 B2 | 6/2010 | Haller et al. | |
| 7,747,329 B2 | 6/2010 | Litvak et al. | |
| 7,801,602 B2 | 9/2010 | McClure et al. | |
| 7,805,198 B2 | 9/2010 | Overstreet et al. | |
| 7,860,570 B2 | 12/2010 | Whitehurst et al. | |
| 7,885,714 B2 | 2/2011 | Loeb | |
| 7,899,539 B2 | 3/2011 | Whitehurst et al. | |
| 2004/0015205 A1 | 1/2004 | Whitehurst et al. | |
| 2004/0152946 A1 * | 8/2004 | Franck | 600/25 |
| 2006/0100672 A1 | 5/2006 | Litvak | |
| 2007/0043403 A1 | 2/2007 | Blamey et al. | |
| 2007/0055308 A1 | 3/2007 | Haller et al. | |
| 2007/0255344 A1 | 11/2007 | Van Dijk | |
| 2007/0260292 A1 | 11/2007 | Faltys et al. | |
| 2010/0121412 A1 | 5/2010 | Litvak et al. | |

FOREIGN PATENT DOCUMENTS

| | | |
|---|---|---|
| WO | 02/09808 | 2/2002 |
| WO | 03/015863 | 2/2003 |
| WO | 03/018113 | 3/2003 |
| WO | 2004/043537 | 5/2004 |
| WO | 2006/053101 | 5/2006 |
| WO | 2007/030496 | 3/2007 |

OTHER PUBLICATIONS

U.S. Appl. No. 60/433,037, filed Dec. 11, 2002, Overstreet.
U.S. Appl. No. 60/523,928, filed Nov. 21, 2003, Litvak.
U.S. Appl. No. 60/665,171, filed Mar. 24, 2005, W.V. Harrison.
U.S. Appl. No. 60/669,822, filed Apr. 5, 2005, K.H. McClure.
U.S. Appl. No. 11/089,171, filed Mar. 24, 2005, Hahn.
U.S. Appl. No. 11/122,648, filed May 5, 2005, Faltys.
U.S. Appl. No. 11/178,054, filed Jul. 8, 2005, Faltys.
U.S. Appl. No. 11/226,777, filed Sep. 13, 2005, Faltys.
U.S. Appl. No. 11/261,432, filed Oct. 28, 2005, Mann.
U.S. Appl. No. 11/262,055, filed Oct. 28, 2005, Fridman.
U.S. Appl. No. 11/386,198, filed Mar. 21, 2006, Saoji.
U.S. Appl. No. 11/387,206, filed Mar. 23, 2006, Harrison.
Harnsberger, et al., "Perceptual "vowel spaces" of Cochlear Implant Users: Implications for the Study of Auditory Adaptation to Spectral Shift". J Acoust Soc Am, vol. 109 (5) pt. 1, pp. 2135-2145, May 2001.
McDermott, et al., "Pitch Ranking with Nonsimultaneous Dual-Electrode Electrical Stimulation of the Cochlea", J Acoust Soc Am, vol. 96(1), pp. 155-162, 2000.
Morse, et al., "The Practical Use of Noise to Improve Speech Coding by Analogue Cochlear Implants", Chaos, Solutions and Fractals, vol. 11(12), pp. 1885-1894, 2000.
Rubinstein, et al., "The Neurophysiological Effects of Simulated Auditory Prosthesis Simulation", Second Quarterly Progress Report NO1-DC-6-2111.
Scheirer, et al., "Construction and Evaluation of Robust Multifeature Speech/Music Discriminator", Acoustics, Speech, and Signal Processing, IEEE International Conference in Munich Germany, pp. 1331-1334, Apr. 21-24, 1997.
Smith, et al., "Chimaeric Sounds, Reveal Dichotomies in Auditory Perception", Nature, vol. 416(6876), pp. 87-90, Mar. 7, 2002.
Van Wieringen, et al., "Comparison of Procedures to Determine Electrical Stimulation Thresholds in Cochlear Implant Users", Ear and Hearing, vol. 22(6), pp. 528-538, 2001.
Zeng, et al., "Loudness of Simple and Complex Stimuli in Electric Hearing", Annals of Otology, Rhinology & Laryngology, vol. 104(9), pp. 235-238, 1995.
Zhang, et al., "Loudness of Dynamic Stimuli in Acoustic and Electric Hearing", J Acoust Soc Am, vol. 102(5) Pt. 1, pp. 2925-2934, Nov. 1997.

* cited by examiner

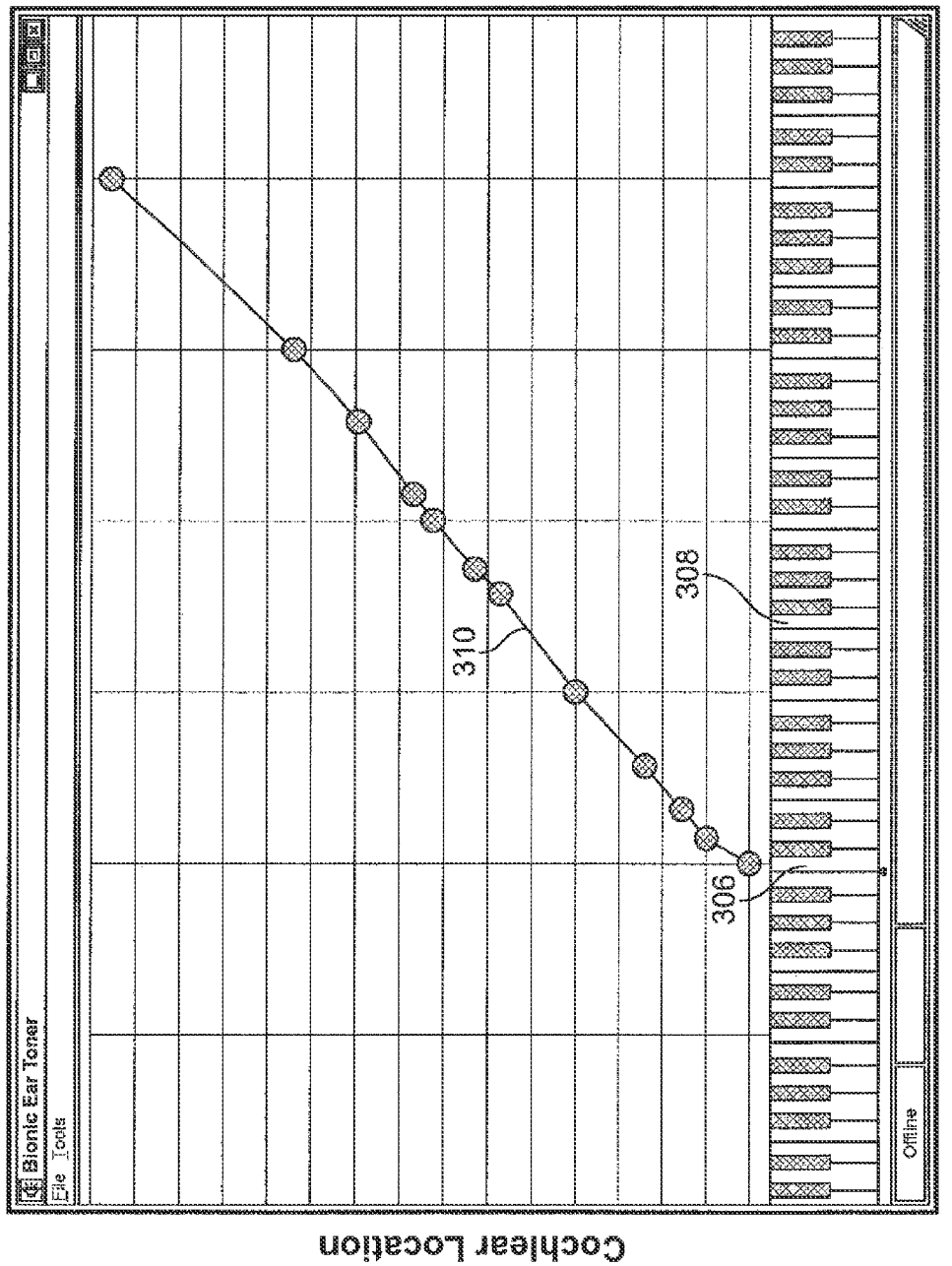

> tuner

806 { One of the number keys (1,2,3,4,5,6,7,8,9,0) contains only ONE note. Each of the other number keys contain TWO notes played at the same time (a chord). Once you found the number key you believe has only ONE note, press "q".

Try all of the notes as many times as you like or not at all.

Hit "RETURN" after any selection.

```
Tuner(1..0,q) > 1   ← 814
Tuner(1..0,q) > 4   ← 816
Tuner(1..0,q) > 2
Tuner(1..0,q) > 8
Tuner(1..0,q) > 5
Tuner(1..0,q) > 6
Tuner(1..0,q) > 3
Tuner(1..0,q) > 4
Tuner(1..0,q) > 8    } 810
Tuner(1..0,q) > 5
Tuner(1..0,q) > 4
Tuner(1..0,q) > 6
Tuner(1..0,q) > 7
Tuner(1..0,q) > 9
Tuner(1..0,q) > 2
Tuner(1..0,q) > q   ← 818
```

The target number was : 7   ← 820
You chose :           2     ← 824 target : 381.46Hz  selected : 346.67Hz
         ‾‾826‾‾              ‾‾830‾‾

ESTIMATED OFFSET= -1.66 semitones (-5 steps)  ← 836

SLOPE= 7.51  ← 834 ans =
    7.5126

FIG. 7

OPTIMIZING PITCH ALLOCATION IN A COCHLEAR STIMULATION SYSTEM

CROSS-REFERENCE TO RELATED APPLICATIONS

This is a continuation of U.S. patent application Ser. No. 11/262,055, filed Oct. 28, 2005, now U.S. Pat. No. 8,027,733, to which priority is claimed and which is incorporated herein by reference in its entirety.

BACKGROUND

The following disclosure relates to cochlear stimulation systems for the treatment of hearing loss and, more particularly, to a method for optimizing pitch allocation using a harmonics-based tuner for aligning the band pass filters associated with an electrode as implemented in a cochlear stimulation system.

Generally, there are two types of hearing loss: conductive and sensorineural. Conductive hearing loss occurs when the normal mechanical pathways for sound to reach the hair cells in the cochlea are impeded, for example, by damage to the ossicles. Conductive hearing loss typically may be treated with the use of a hearing aid system, which amplifies sound so that acoustic information can reach the cochlea and the hair cells, or through surgical procedures. Hearing aids, however, are not effective for treating sensorineural hearing loss, no matter how loud the acoustic information is amplified, given the hair cells in the cochlea are either absent or destroyed.

Sensorineural hearing loss occurs when the hair cells in the cochlea, which are needed to transduce acoustic signals into auditory nerve impulses, are either absent or destroyed. Sensorineural hearing loss typically may be treated with a cochlear stimulation system, such as the systems described in U.S. Pat. Nos. 5,938,691 and 6,219,580, each of which is incorporated herein by reference. These cochlear stimulation systems produce sensations of sound in patients with sensorineural hearing loss by direct electrical stimulation of the ganglia of the auditory nerve cells. These systems bypass the defective cochlea hair cells that normally transduce acoustic energy into electrical activity in such nerve cells, leading to perception of sound in the patient's brain.

Cochlear stimulation systems typically include an electrode array, an implantable cochlear stimulator ("ICS"), an externally wearable signal processor (or speech processor, portions of which can be implanted) and a microphone. The speech processor generally employs a headpiece that holds the microphone to be positioned adjacent to the patient's ear. In operation, the electrical stimulation applied to the ganglia is derived from acoustic signals received by the microphone and transformed into control data by the speech processor that is programmed during a fitting process to meet the particular requirements of each patient. The speech processor transmits the control data to the ICS, which uses the control data to selectively generate electrical stimuli and to apply the electrical stimuli to one or more cochlea stimulating channels, each associated with an individual electrode or a pair or group of electrodes within or on the electrode array, which is typically surgically inserted into the patient's cochlea.

Within the cochlea, there are two main cues that convey "pitch" (frequency) information to the patient. They are (1) the place or location of stimulation along the length of a cochlear duct and (2) the temporal structure of the stimulating waveform. Because each place along the cochlea corresponds to a specific perceived sound frequency, the relationship between the cochlear place and perceived sound frequency is typically different for every individual as no two cochleas are alike and the nerve wiring between the cochlea and to the brain is different for every individual. In the cochlea, received sound frequencies are mapped to a "place" in the cochlea, generally from high to low sound frequencies from the basilar to apical direction.

At present, many patients fitted with a cochlear stimulation system find it difficult to enjoy music generally because the mapping of the electrode array in a cochlear duct to the perceived audio frequencies is not correct. Correctly mapping an electrode array in a cochlear duct to the perceived audio frequencies is complicated by differences in a patient's anatomy as mentioned above. Often times, when the electrode array is surgically inserted into a patient's cochlea, the final implanted position of the electrode array is misaligned with the proper place along the patient's cochlea. Moreover, the nuances of the electric field propagation at each electrode contact in the electrode array tends to be variable. Both the misalignment of the electrode contacts and variability of the electric field propagation leads to an arbitrariness to a mapping scheme between the electrode contact and the perceived sound frequency—i.e., the perceived sound frequencies are not the same as the correct received sound frequencies. Conventional fitting programs that process delivery of certain received sound frequencies through a selected electrode contract or electrode contacts typically do not compensate for this misalignment and variableness.

U.S. Pat. No. 7,702,396, incorporated herein by reference, attempts to overcome these problems by providing an improved fitting tool to better convey pitch information to a user of a cochlear implant. The disclosed methods and systems provide a fitting routine using melodies to help properly map specific electrodes and/or "places" on the cochlear to corresponding perceived audio frequencies. The use of melodies, however, for tuning or mapping tends to be problematic for those users having poor auditory memory or musical training.

SUMMARY

The present inventors recognized that that an improved fitting tool was needed, particularly for those patients with poor auditory memory, to correctly and more easily map or tune misaligned electrode contacts to the perceived sound frequencies. The present inventors also recognized that the precise position of each electrode contact of the implanted electrode array could be adjusted or aligned by changing the center frequency of a BPF associated with each electrode, but that the determination of which center frequency to start at and the necessary change to the center frequency typically is not easy and is typically estimated at the outset for each patient, which also tends to be inaccurate for that patient. Consequently, the present inventors developed systems and techniques that utilize a harmonics-based tuner for adjusting the center frequencies of the BPF(s) associated with each implanted electrode contact to easily and correctly map each implanted electrode contact to the perceived audio frequencies. In general, the patient is allowed to listen to various predetermined harmonic-based sounds, all but one will sound like a chord, while one will sound like a single note. The patient's task is to pick the sound that sounds like a single note. The implant fitting line and slope (mm/octave) that corresponds to the single note sound describes the actual position of the implanted electrode array. The center frequencies of the BPF(s) associated with each implanted electrode contact are then adjusted based on the determined implant fitting slope.

Implementations of the system and techniques described here may include various combinations of the following features.

A technique to fit a cochlear implant system may include implanting an electrode array having a plurality of electrodes into the cochlea of a user, where the electrode array has an associated implant fitting characteristic that defines a relationship between the implanted electrode array and audio frequencies, presenting sounds to the user through the electrode array, wherein each sound includes a fundamental frequency and harmonics, receiving from the user a selection of one of the sounds that most closely conforms to a single note, and determining a slope of the implant fitting characteristic of the electrode array based on the sound selected by the user. The technique may also include changing a center frequency of a band pass filter associated with each electrode based on the determined slope. The step of presenting the sounds to the user through the electrode array may include presenting repetitively the sounds to the user by pressing keys of a keyboard or keypad, where each key is associated with one of the sounds.

A technique to tune a filter associated with an intra-cochlear electrode may include defining a plurality of audio presentations (where each audio presentation includes a fundamental frequency and harmonics), presenting the defined audio presentations to a patient, receiving from the patient a selection of an audio presentation that most closely sounds like a single note, and adjusting a center frequency of the filter based on the selected audio presentation. The step of presenting the defined audio presentations to the patient may be initiated by pressing keys of a keyboard or keypad, each key being associated with one of the defined audio presentations. The step of adjusting the center frequency of the filter based on the selected audio presentation may include determining a slope of the intra-cochlear electrode based on the selected audio presentation.

A cochlear implant fitting system may include an implantable cochlear stimulator, an electrode array having a multiplicity of electrodes connected to the implantable cochlear stimulator, and a means for generating a sound including a fundamental frequency and a plurality of harmonics delivered through the electrode array. The cochlear implant system may also include a means for adjusting a slope of an implant fitting line embodied in presenting the sound, and a means for adjusting an offset of the implant fitting line.

The systems and techniques described here may provide one or more of the following advantages. The techniques may be performed quickly and easily in a clinical setting and yield an accurate result of the implant fitting line and slope of an inserted electrode array. Moreover, the use of the harmonics-based tuner may be utilized with fitting software to allow easier and better tuning of the processing software for a patient. Hence, the use of currently available fitting systems, such as SOUNDWAVE™ from ADVANCED BIONICS® Corporation, to allow the dynamic manipulation of the BPFs during the filter alignment process may be possible.

Details of one or more implementations are set forth in the accompanying drawings and the description below. Other features and advantages will be apparent from the description and drawings, and from the claims.

DESCRIPTION OF DRAWINGS

FIG. 4 represents the linear relationship of musical notes to places along an individual's cochlea.

FIG. 7 depicts an example of a menu interface to a computer software program that may be used to implement the steps described in FIG. 6.

Like reference symbols in the various drawings indicate like elements.

DETAILED DESCRIPTION

The following disclosure describes a tool to better determine the implant fitting line, or characteristic, and slope for a cochlear stimulation system. A harmonics-based tuning method may be used to properly map specific electrodes and/or "places" on the cochlea to corresponding perceived audio frequencies. This mapping may be referred to as an "implant fitting line" (or implant fitting characteristic) and depends in particular on the type of electrode array used, the type of cochlear stimulation system, and the patient's anatomical variation. From the implant fitting line, the slope (mm/octave) may be determined. When the implant fitting line is properly determined and implemented in a cochlear stimulation system, the patient typically is able to experience a significant improvement in the perceived quality of sound, particularly with music and speech.

Figure 1:
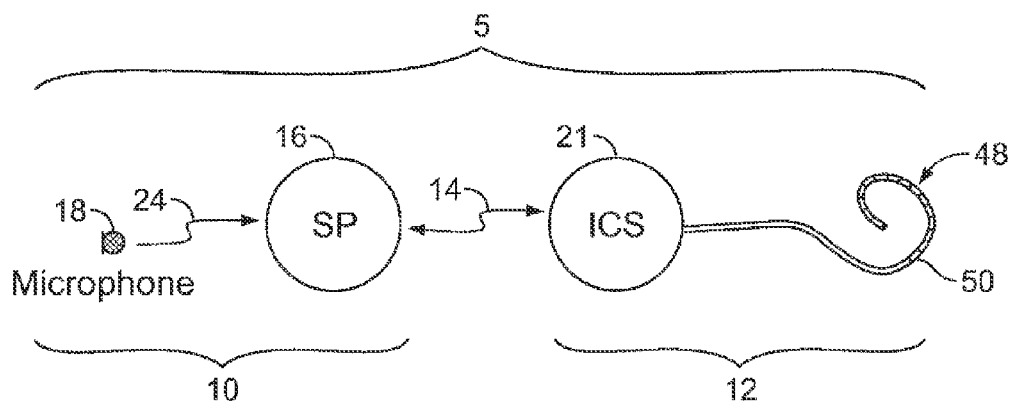
FIG. 1 shows a typical cochlear stimulation system in which the harmonic-based tuner and techniques may be implemented.

FIG. 1 depicts one implementation of a cochlear stimulation system in which the harmonic-based tuning method may be implemented. The system includes a speech processor portion 10 and a cochlear stimulation portion 12. The speech processor portion 10 includes a speech processor (SP) 16 and a microphone 18. The microphone 18 may be connected directly to the SP 16 or may be coupled to the SP 16 through an appropriate communication link 24. The cochlear stimulation portion 12 includes an implantable cochlear stimulator (ICS) 21 and an electrode array 48. The electrode array 48 is typically adapted to be inserted within a duct of the cochlea. The array 48 includes a multiplicity of electrodes 50, e.g., sixteen electrodes spaced along its length that are selectively connected to the ICS 21. The electrode array 48 may be substantially as shown and described in U.S. Pat. No. 4,819, 647 or U.S. Pat. No. 6,129,753, incorporated herein by reference. Electronic circuitry within the ICS 21 allows a specified stimulation current to be applied to selected pairs or groups of the individual electrodes included within the electrode array 48 in accordance with a specified stimulation pattern, defined by the SP 16.

The ICS 21 and the SP 16 are shown as linked together electronically through a suitable data or communications link 14. In some cochlear stimulation systems, the SP 16 and microphone 18 comprise the external portion of the cochlear stimulation system and the ICS 21 and electrode array 48 comprise the implantable portion of the system. Thus, the data link 14 may be a transcutaneous (through the skin) data link that allows power and control signals to be sent from the SP16 to the ICS 21. In some implementations, data and status signals may also be sent from the ICS 21 to the SP 16.

Typically, where a transcutaneous data link must be established between the external portion and the implantable portions of the system, such link is realized by an internal antenna coil within the implantable portion and an external antenna coil within the external portion. In use, the external antenna coil is aligned over the location where the internal antenna coil is implanted, allowing such coils to be inductively coupled to each other, thereby allowing data, e.g., the magnitude and polarity of a sensed acoustic signals and power to be transmitted from the external portion to the implantable portion. Note, in other implementations, both the SP 16 and the ICS 21 may be implanted within the patient, either in the same housing or in separate housings. If in the same housing, the link 14 may be realized with a direct wire connection within such housing. If in separate housings, as taught, e.g., in U.S. Pat. No. 6,067,474, incorporated herein by reference, the link 14 may be an inductive link using a coil or a wire loop coupled to the respective parts.

The microphone 18 senses acoustic signals and converts such sensed signals to corresponding electrical signals and may thus be considered an acoustic transducer. The electrical signals are sent to the SP 16 over a suitable electrical or other link 24. The SP 16 processes these converted acoustic signals in accordance with a selected speech processing strategy to generate appropriate control signals for controlling the ICS 21. Such control signals specify or define the polarity, magnitude, location (which electrode pair or electrode group receive the stimulation current), and timing (when the stimulation current is applied to the electrode pair) of the stimulation current that is generated by the ICS. Such control signals thus combine to produce a desired spatio-temporal pattern of electrical stimuli in accordance with the desired speech processing strategy. Unlike earlier cochlear stimulation systems, more recent cochlear stimulation systems confine such control signals to circuitry within the implantable portion of the system, thereby avoiding the need to continually send or transmit such control signals across a transcutaneous link.

The speech processing strategy is used, among other reasons, to condition the magnitude and polarity of the stimulation current applied to the implanted electrodes 50 of the electrode array 48. Such speech processing strategy involves defining a pattern of stimulation waveforms that are to be applied to the electrodes as controlled electrical currents.

Analog waveforms used in analog stimulation patterns are typically reconstructed by the generation of continuous, short monophasic pulses (samples). The sampling rate is selected to be fast enough to allow for proper reconstruction of the temporal details of the signal. An example of such a sampled analog stimulation pattern is a simultaneous analog sampler (SAS) strategy.

Figure 2:
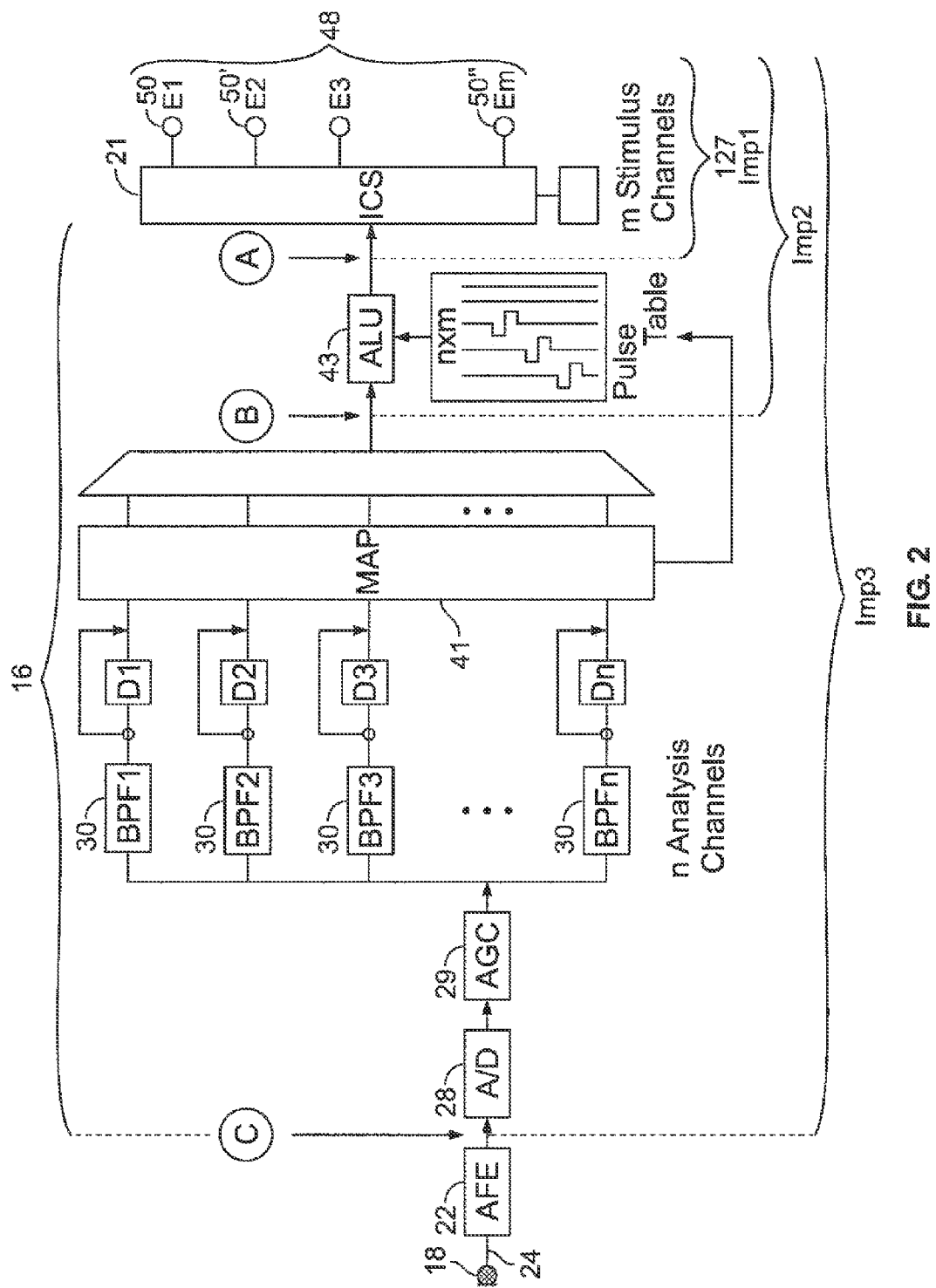
FIG. 2 depicts a partial functional block diagram of a cochlear stimulation system, in which the harmonic-based tuner and techniques may be implemented.

FIG. 2 shows a partial functional block diagram of the SP 16 and the ICS 21 of an exemplary cochlear stimulation system in which the harmonic-based tuner may be implemented. A complete description of the functional block diagram of this cochlear stimulation system may be found in U.S. Pat. No. 6,219,580 ('580 patent), which is incorporated herein by reference. In the manner described in the '580 patent, the cochlear stimulation system functionally shown provides n analysis channels that may be mapped to one or more stimulus channels. That is, after the incoming sound signal is received through the microphone 18 and the analog front end circuitry (AFE) 22, it is digitized in an analog to digital (A/D) converter 28 and then subjected to appropriate gain control (which may include compression) in an automatic gain control (AGC) unit 29. After appropriate gain control, the signal is divided into n analysis channels, each of which includes a band pass filter, BPFn 30, centered at a selected frequency. The signal present in each analysis channel is processed as described more fully in the '580 patent or as is appropriate using other signal processing techniques and the signals from each analysis channel are then mapped, using mapping function 41, so that an appropriate stimulus current of a desired amplitude and timing, may be applied through a selected stimulus channel to an electrode contact to stimulate the auditory nerve. Thus, the information contained in the n "analysis channels" is appropriately processed, compressed and mapped in order to control the actual stimulus patterns that are applied to the patient by the ICS 21 and its associated electrode array 48.

The electrode array 48 includes a multiplicity of electrode contacts 50, connected through appropriate conductors to respective current generators or pulse generators within the ICS. Through these multiplicity of electrode contacts, a multiplicity of stimulus channels, e.g., m stimulus channels, exist through which individual electrical stimuli may be applied at m different stimulation locations or places within the patient's cochlea or other tissue stimulation site.

While it is common to use a one-to-one mapping scheme between the analysis channels and the stimulus channels, wherein n=m, and the signal analyzed in the first analysis channel is mapped to produce a stimulation current at the first stimulation channel, and so on, it is not necessary to do so. Instead, in some instances, a different mapping scheme may prove beneficial to the patient. For example, assume that n is not equal to m (n, for example, could be at least 20 or as high as 32, while m may be no greater than sixteen, e.g., 8 to 16). The signal resulting from analysis in the first analysis channel may be mapped, using appropriate mapping circuitry 41 or equivalent, to the first stimulation channel via a first map link, resulting in a first stimulation site (or first area of neural excitation). Similarly, the signal resulting from analysis in the second analysis channel of the SP 16 may be mapped to the second stimulation channel via a second map link, resulting in a second stimulation site. Also, the signal resulting from analysis in the second analysis channel may be jointly mapped to the first and second stimulation channels via a joint map link. This joint link results in a stimulation site that is somewhere in between the first and second stimulation sites.

The "in-between" site at which a stimulus is applied may be referred to as a "stimulation site" produced by a virtual electrode. This capability of using different mapping schemes between n analysis channels and m stimulation channels to thereby produce a large number of virtual and other stimulation sites provides flexibility with respect to positioning the neural excitation areas precisely in the cochlear place that best conveys the frequencies of the incoming sound. Through appropriate weighting and sharing of currents between two or more physical electrodes, it is possible to provide a large number of virtual electrodes between physical electrodes, thereby effectively steering the location at which a stimulus is applied to almost any location along the length of the electrode array.

The output stage of the ICS 21, which connects with each electrode E1, E2, E3, ... Em of the electrode array, may be as described in U.S. Pat. No. 6,181,969, which is incorporated herein by reference. Such an output stage provides a programmable N-DAC or P-DAC (where DAC stands for digital-to-analog converter) connected to each electrode so that a programmed current may be sourced to the electrode or sunk from the electrode. Such configuration allows any electrode to be paired with any other electrode and the amplitudes of the currents may be programmed and controlled to gradually shift the stimulating current that flows from one electrode through the tissue to another adjacent electrode or electrodes, thereby providing the effect of "shifting" the current from one or more electrodes to another electrode(s). Through such current shifting, the stimulus current may be shifted or directed so that it appears to the tissue that the current is coming from or going to an almost infinite number of locations.

The speech processing circuitry 16 generally includes all of the circuitry from point (C) to point (A). In prior art cochlear stimulation systems, the entire SP circuitry was housed in a speech processor that was part of the external (or non-implanted) portion of the system. That is, in such prior art systems, only the ICS 21 and its associated electrode array were implanted, as indicated by the bracket labeled "Imp1" (for "Implant-1"). This means that in such prior art systems, the signal passing through the serial data stream at point (A) is also the signal that must pass through the transcutaneous communication link from the external unit to the implanted unit. Because such signal contains all of the defining control data for the selected speech processing strategy for all m stimulation channels, it therefore has a fairly high data rate associated therewith. As a result of such high data rate, either the system operation must be slowed down, which is generally not desirable, or the bandwidth of the link must be increased, which is also not desirable because the operating power increases.

In contrast to prior art systems, a modern cochlear stimulation system, such as the CII Cochlear Stimulation System manufactured by ADVANCED BIONICS® Corporation of Sylmar, Calif., advantageously puts at least a portion of the speech processor 16 within the implanted portion of the system. For example, a cochlear stimulation system may include the Pulse Table and arithmetic logic unit (ALU) 43 inside of the implanted portion, as indicated by the bracket labeled "Imp2." Such partitioning of the speech processor 16 offers the advantage of reducing the data rate that must be passed from the external portion of the system to the implanted portion. That is, the data stream that must be passed to the implanted portion Imp2 comprises the signal stream at point (B). This signal is essentially the digitized equivalent of the modulation data associated with each of the n analysis channels, and (depending upon the number of analysis channels and the sampling rate associated with each) may be significantly lower than the data rate associated with the signal that passes through point (A). Hence, improved performance without sacrificing power consumption may be obtained with such a cochlear implant.

Future generations of cochlear stimulation systems may incorporate more and more of the speech processor 16 within the implanted portion of the system. For example, a fully implanted speech processor 16 would incorporate all of the SP in the implanted portion, as indicated by the bracket labeled Imp3. Such a fully implanted speech processor offers the advantage that the data input into the system, i.e., the data stream that passes through point (C), would need only have a rate commensurate with the input acoustic signal.

Additional features made possible by the cochlear stimulation system shown in FIG. 2 or equivalents, which may be used in conjunction with the presently described harmonics-based tuner, allow the current stimuli to be applied to the target tissue at fast rates and in a way that more naturally elicits a stochastic firing of the target tissue.

Figure 3:
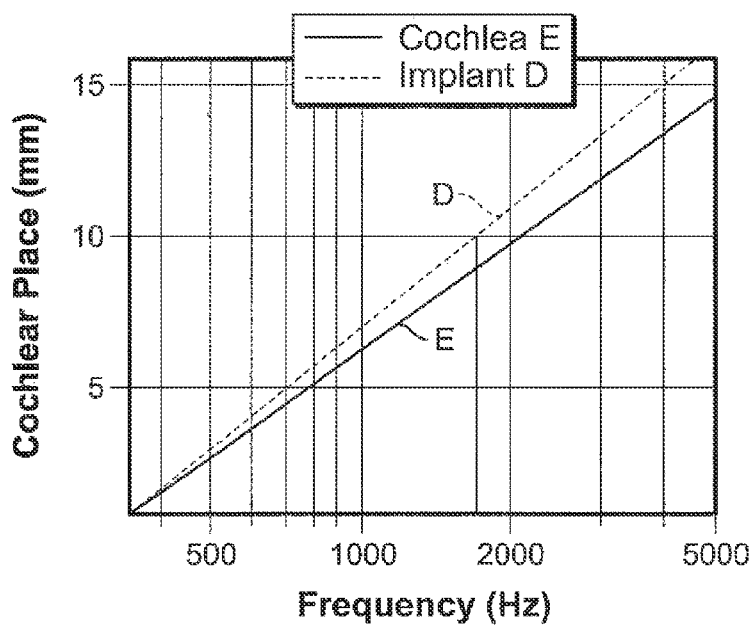
FIG. 3 illustrates the intrinsic line of an individual's cochlea and an implant fitting line, or characteristic, showing both lateral and absolute misalignment.

FIG. 3 illustrates the intrinsic line, or characteristic, of an individual's cochlea and an implant fitting line showing both lateral and absolute misalignment. The line E may be referred to as the "intrinsic line" having an "intrinsic slope" for a patient's cochlea. The intrinsic line E, which is the lower line, represents the actual relationship between the cochlear place (mm) versus the associated log (frequency of the perceived sound of that place). In an individual's ear, each place along the cochlea corresponds to a specific perceived sound frequency. This relationship between cochlear place and perceived sound frequency is typically different for every individual, since no two cochleas are alike and the nerve wiring between the cochlea and to the brain is different for every patient. The slope of the intrinsic line E may be calculated, where the slope is the change in cochlear place over the change in log (frequency of the perceived sound of that place).

The implant fitting line D, which is the upper line, represents the implant fitting line of the cochlear stimulation system. The implant fitting line D, which maps the electrode place versus log (frequency of the perceived sound), is typically also different for every patient. As can be seen, the implant fitting line is misaligned with the intrinsic line E. To properly perceive sounds, as produced through a particular cochlear stimulation system, including a specific electrode array, the system must be "fitted" or "tuned" to accommodate the individual anatomical differences, the particular configuration of the electrode array, and the electrode.

Assume that a 2000 Hz incoming sound is picked up (or delivered) by the cochlear stimulation system. The patient then should perceive a 2000 Hz tone but that is not typically the case. After the electrode array is implanted, an estimate is typically made for what the correct implant fitting line D (including slope) should be. The slope of the implant fitting line D is the change in electrode distance (corresponding to a particular electrode place) over the change in log (frequency of the perceived sound at that place). Because of variability in an individual's anatomical cochlea, invariably the estimated implant fitting line D (and slope) will not initially correspond to the intrinsic line E. The goal is to adjust (tune) the implant fitting line D to match or overlap the intrinsic line E, or at least to have the same slope as intrinsic line E, such that a harmonic-relationship between the two lines is established, i.e., even if the implant fitting line D does not overlap the intrinsic line E, a musical tune typically will be recognized, as each note in relationship to other notes in a tune are generally in a harmonic relationship.

As seen in FIG. 3, stimulation must be applied at a slightly different cochlear place than was originally guessed to yield a perceived frequency of 2000 Hz. For example, the electrode and cochlear place to be stimulated is at about 11 mm for the intrinsic line D, not the predicted 10 mm for the implant fitting line E. Such pitch warping makes enjoyment of music difficult. However, if the electrode array position in the cochlea is altered slightly, either placed further into the cochlea or slightly out from the cochlea, the relationship of each "place" along the electrode array would again change in relationship. Thus, to determine the slope of the electrode array "place" along the electrode array and the corresponding perceived audio frequency, the electrode array typically must be adjusted during the fitting procedure.

FIG. 4 represents, in a simplified way, the relationship of musical notes to cochlear place. A place on the cochlea corresponds to notes on a musical scale, as represented by notes on a piano scale. Music theory teaches that there are twelve semitones per octave, i.e., there are twelve notes (e.g., piano keys) between a C note 306 on one octave and a C note 308 on the next higher octave. As can be seen, the line 310 formed by the notes over four octaves is nearly linear. As a result, determining the correct implant fitting slope (in mm/octave), which results in a fitting line that is parallel to the intrinsic line, will help a patient hear and appreciate music.

Figure 5A:
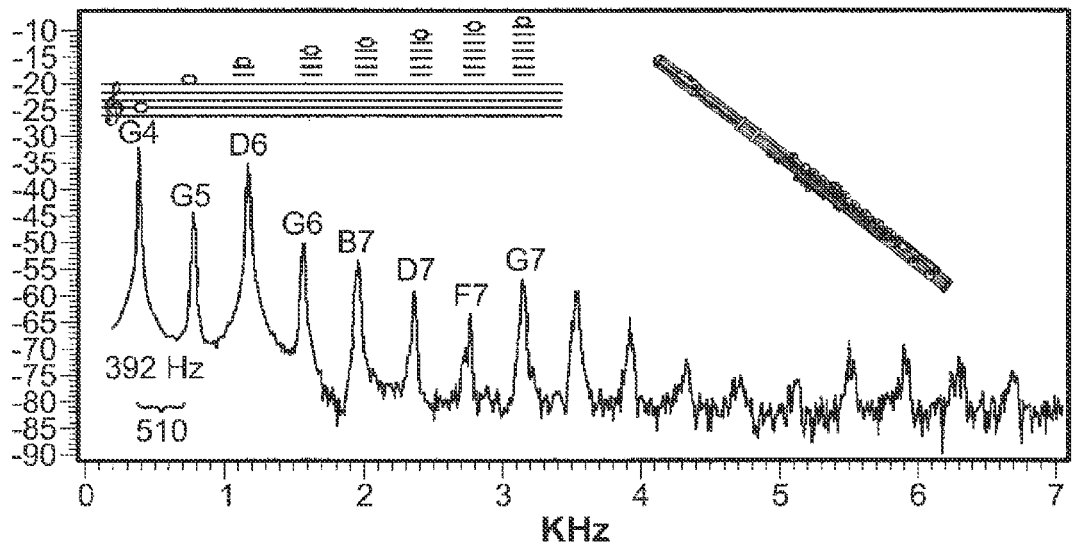
FIGS. 5A and 5B illustrates the harmonic relationship between notes played on one instrument (a flute in FIG. 5A) and the same notes played on another instrument (a violin in FIG. 5B).
Figure 5B:
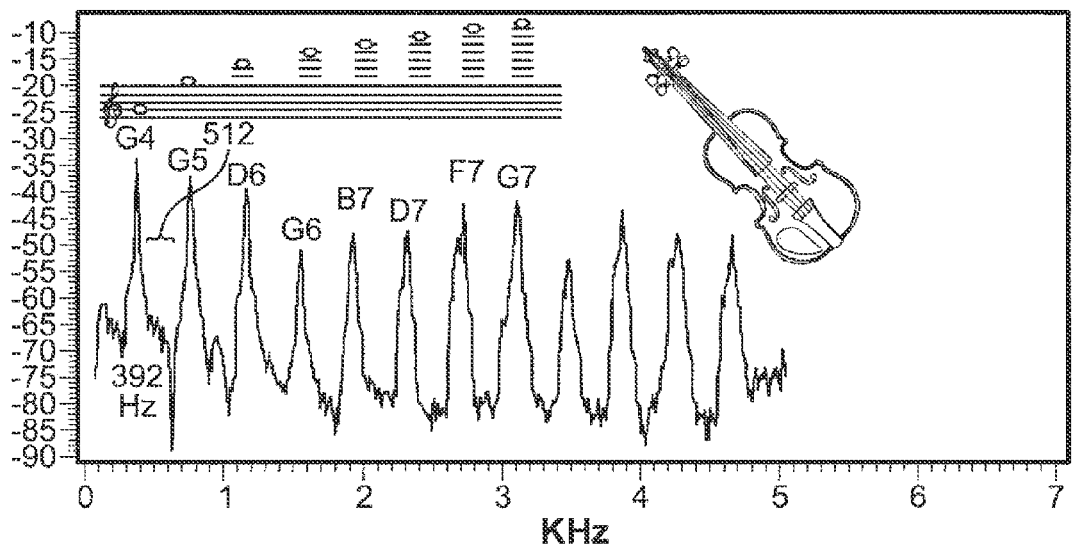

FIGS. 5A and 5B illustrates the harmonic relationship between notes played on one instrument (a flute in FIG. 5A) and the same notes played on another instrument (a violin in FIG. 5B) is illustrated. Generally, each musical note has a tone having a fundamental frequency F1 and subsequent harmonics that are multiples of the tone, i.e., a second harmonic having a frequency 2*F1, a third harmonic having a frequency 3*F1, and so on. The harmonics associated with a particular note generally have an amplitude substantially smaller than the amplitude of the tone of the note. Also, generally the difference between a note on one instrument (e.g., a flute) and the same note on a different instrument (e.g., a violin) is the relative amplitude of the harmonics.

For example, in comparing the note G4, having a fundamental frequency of 392 Hz, played on a flute (as shown in FIG. 5A) to the same note played on a violin (as shown in FIG. 5B), the main differences are the relative amplitudes of the harmonics. In this example, the amplitudes of the harmonics 510 of the note G4 played on the flute are much smaller than the amplitudes of the harmonics 512 of the note G4 played on the violin. Even with these differences in harmonics, in both the flute and the violin, the only note heard is G4. Thus, the harmonics of a particular note may be used to determine the correct implant fitting slope (in mm/octave) for the band pass filters used for each implanted electrode contact.

Figure 6:
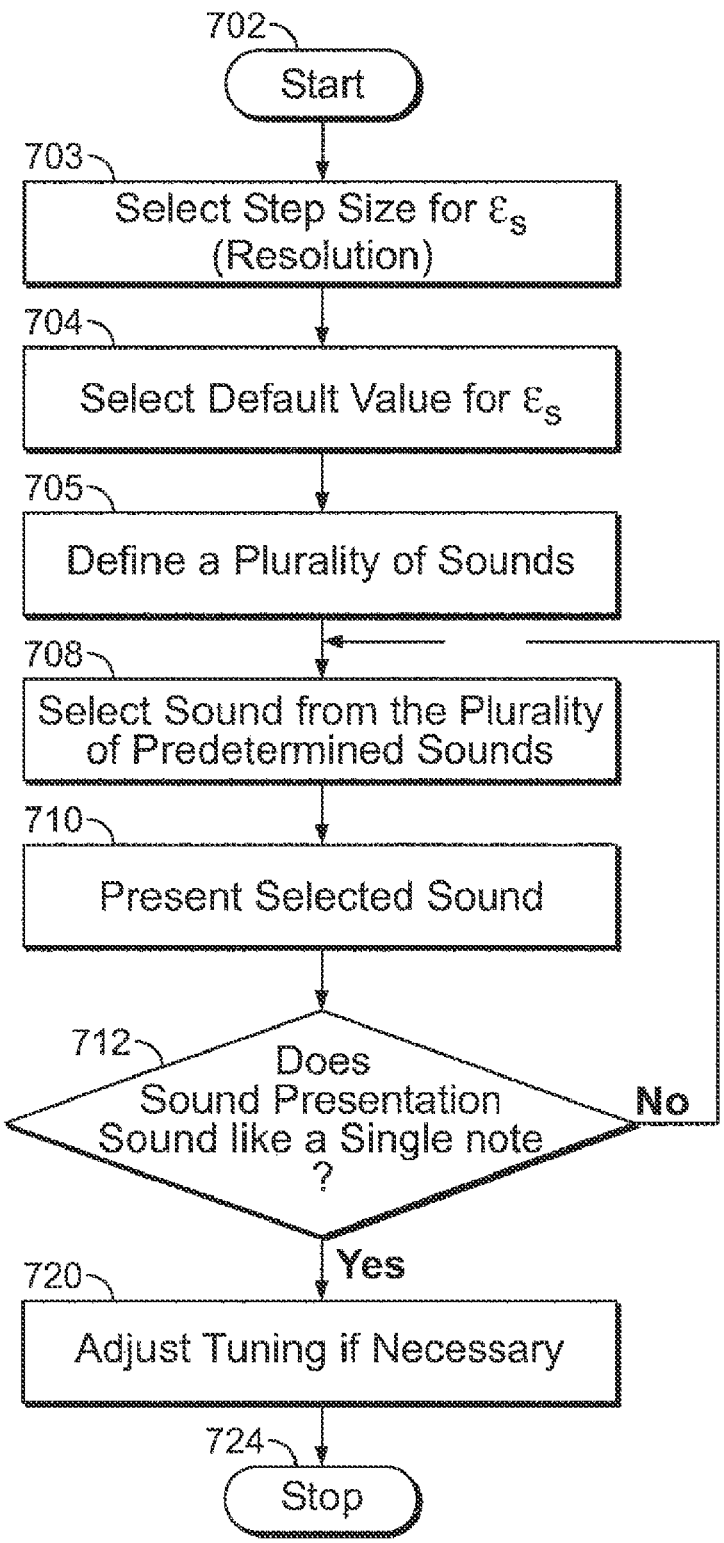
FIG. 6 depicts in flow chart form an implant fitting routine utilizing a harmonics-based tuner and technique for aligning the band pass filters associated with each implanted electrode contact so as to permit the correct mapping of the implanted electrode array to the perceived audio frequencies.

FIG. 6 depicts in flow chart form an implant fitting routine utilizing a harmonics-based tuner and technique for aligning the band pass filters associated with each implanted electrode contact so as to permit the correct mapping of the implanted electrode array to the perceived audio frequencies. To correctly map the electrode array to the perceived audio frequencies, the patient's implant fitting slope typically must be determined, which as noted above, generally is a difficult task because the implant fitting slope depends on the patient's anatomy, the electrode array configuration used, and the position of the electrode array relative to the cochlea. The tuner fitting routine herein utilizes a harmonics-based tuner for determining the implant fitting slope for a particular patient.

The fitting routine utilizing the harmonics-based tuner may be implemented in software and include a graphical user interface and input device, such as keyboard or mouse. Generally, the fitting routine allows a patient fitted with a cochlear stimulation system to select which sound from a plurality of predetermined sounds, e.g., ten sounds of predetermined duration (such as 1 to 2 seconds), is presented by pressing one of the digit keys 0-9 on a keyboard or key pad.

Each keyboard digit key may be associated with a different predetermined sound. Each predetermined sound may be a different complex of the harmonics of an arbitrary note (e.g., a C note) and is based on a different slope (e.g., mm/octave).

In this implementation, the complexes included the fundamental frequency and four harmonics of the note. In other implementations more or fewer harmonics may be used to comprise the complex. One of these complexes generally will sound like a single note to a normal (i.e., unassisted) hearing listener (which may be referred to as the actual target sound), but to a patient fitted with a cochlear stimulation system, the sound presentation would generally sound like a chord (e.g., two or more notes in harmonic relationship) due to the electrode array misalignment. Likewise, the other complexes will generally sound like a chord to a normal hearing listener, but to a patient fitted with a cochlear stimulation system, one of these other complexes will generally sound like a single note (which may be referred to as the perceived target sound). The perceived target sound will have a slope that corresponds to the actual implant fitting slope of the electrode array. The actual implant fitting slope may then be used to determine how much to adjust the center frequencies of the band pass filters associated with the electrode contacts. This may done using ADVANCED BIONICS® SOUNDWAVE™ fitting software.

To determine the harmonics that make of the various complexes, it is useful to know the slope effect on center frequencies of a cochlear place. The frequencies along the cochlea may be approximated by the following equation, which relates the center frequency of one cochlear place ($CF_1$) to that of another ($CF_m$), where m is the distance in millimeters along the cochlea from the location of $CF_1$, and S is the slope in form of octaves/mm:

$$CF_m = CF_1(2^{mS}) \tag{1}$$

In the default case of the cochlea (i.e., for an unassisted hearing listener), S may be estimated to be the default value of $S=S_d=0.25$ octaves/mm. If the electrode contact deviates from the default, the slope may be described as:

$$S=S_d+\epsilon_s, \tag{2}$$

where $\epsilon_s$ is the deviation in octaves/mm.

The harmonics of a fundamental frequency ($f_0$) of a note are defined as the integer multiples of $f_0$. To form the complex of harmonics of an arbitrary note, the harmonics that are chosen are those defined by the following equation:

$$f_h = f_0(2^h), \tag{3}$$

where h is an integer.

Given the identical form of equations (1) and (3), a harmonic of the fundamental frequency ($f_0$) of a particular note that corresponds to integer h along the basilar membrane of the cochlear may be located, i.e., the cochlear place of any harmonic may be found along the basilar membrane of the cochlea. The cochlear place (m) of any harmonic corresponding to h, may be found along the basilar membrane of the cochlea according to the following equations:

$$h = mS; m = \frac{h}{S} \tag{4}$$

The harmonics of the arbitrary note may be "remapped" to correspond to the actual electrode position, and the slope is changed by some value $\epsilon_s$ (in octaves/mm). One way of looking at this problem is that the harmonic corresponding to h will shift. If $h_d$ is the default harmonic and the "shifted" harmonic is $h_d'$ then, $$h_d' = mS = m(S_d + \varepsilon_s) = h_d + \frac{\varepsilon_s h_d}{S_d} \quad (5)$$

The modified frequencies of the harmonics then are:

$$f_{h_d}' = f_0\left(2^{h_d + \frac{\varepsilon_s h_d}{S_d}}\right) \quad (6)$$

Thus, for any change $\varepsilon_s$ in the slope, a collection of perceived harmonics of the fundamental frequency ($f_0$) may be determined. In a normal hearing person (i.e., an unassisted hearing listener), $\varepsilon_s$ is 0, and equation (6) reduces to the relation shown in equation (3). Therefore, equation (6) may be used to create the various different complexes of the predetermined sounds, each of which may be assigned to a particular digit key on a keypad or keyboard.

As an example, a predetermined sound may be represented by the following complex in frequency space:

$$C = w_0\delta(f_0) + w_1\delta(f_1) + w_2\delta(f_2) + w_3\delta(f_3) + w_4\delta(f_4), \quad (7)$$

where $w_i$ is the amplitude of a given harmonic i, $f_i$ is the frequency of that harmonic, and $\delta(f_i)$ is the delta function at the frequency $f_i$.

As stated above, the fundamental frequency ($f_0$) is used in each complex and corresponds to the default center frequency of the first filter. In this example, $f_0$ is 371 Hz. In the normal complex (i.e., $\varepsilon_s$=0 and $S_d$=0.25 octaves/mm) the frequencies comprising the complex ($f_{0-4}$) computed using equation (6) are 371 Hz, 742 Hz, 1484 Hz, 2968 Hz and 5936 Hz, respectively. In a shifted complex (e.g., with $\varepsilon_s$=0.083 octaves/mm), the frequencies comprising the complex ($f_{0-4}$) computed using the equation (6) are 371 Hz, 935 Hz, 2355 Hz, 5934 Hz and 14952 Hz, respectively. Other shifted complexes may be created by changing $\varepsilon_s$. In this implementation, $\varepsilon_s$ may be selected between −0.5 octave/mm and 0.5 octave/mm, i.e., −0.5<$\varepsilon_s$<0.5.

The keyboard digit key associated with the actual target sound may be considered the target key, which may be automatically changed randomly each time the implant fitting routine starts. Depending on the tuner frequency resolution, the harmonics associated with each digit key may get further apart or closer together going away from the target key. Thus, the patient's task is to press the digit keys in any order, listen to the sound generated as a result of pressing a particular digit key, and choose the sound that sounds most like a single note as opposed to a chord.

The implant fitting routine starts at block 702 and then proceeds to the first operation, represented by box 703, where the audiologist or patient may select the frequency resolution of the tuner (the step by which $\varepsilon_s$ will change for each key or button), where a larger number may indicate a "fine" frequency resolution and a smaller number may represent a "coarse" frequency resolution. The selected resolution effects how far apart ("coarse resolution") or closer together ("fine resolution") the harmonics are with respect to each predetermined sound. In alternative implementations, the operation represented by box 703 need not be implemented. Next as shown in box 704, the audiologist or patient defines the default value for $\varepsilon_s$. Here, $\varepsilon_s$ typically will be 0. Next as shown in box 705, the audiologist or patent defines a plurality of sounds, e.g., one sound mapped to each digit key of a keypad or keyboard.

As shown in box 708, the patient selects a sound to be presented from one of the ten predetermined sounds defined in box 705, e.g., by pressing one of the digit keys on a keyboard. Next, as shown in box 710, the selected sound is presented to the patient. As noted above, the patient is previously fitted with a cochlear stimulation system, which processes the received sound and stimulates the cochlea. Then, as shown in box 712, after the patients listens to the sound, the patient determines whether the perceived sound presentation sounds like a single note or a chord. When the target key is pressed, e.g., and the patient determines that the sound presentation does not sound like a single note, then this is an indication that the cochlear stimulation system is mistuned (i.e., the implanted electrode array is misaligned with the cochlear place), as the patient is actually hearing different frequencies than those that are actually being delivered to the patient. As mentioned previously, the predetermined sound associated with the target key would sound like a single note to a normal hearing listener.

In the event the patient determines the sound presentation does not sound like a single note, but sounds more like two or more notes, the process proceeds to box 708, where the patient selects another sound to be presented, by, e.g., pressing another digit key. This process is iterative until the patient determines the sound presentation sounds like a single note (i.e., the perceived target sound), at which point the pitch allocation in the patient's cochlear stimulation system is likely optimized or close to being optimized and the implant fitting slope may then be determined and the band pass filters associated with each of the electrodes of the electrode array may be adjusted based on the determined slope, as shown in box 720.

Once the patient determines which sound presentation sounds like a single note (i.e., the perceived target sound), the implant fitting slope may be determined based on the $\varepsilon_s$ associated with the sound presentation that the patient determined sounded like a single note and equation (2), i.e., where the implant fitting slope is equal to ($S_d + \varepsilon_s$). Here, the implant fitting slope is adjusted uniformly across the entire electrode array. Based on this uniform implant fitting slope, each band pass filter may be adjusted or tuned to correctly map the implanted electrode array to the perceived audio frequencies. For example, the determined implant fitting slope may be provided as input to a cochlear fitting software, such as SOUNDWAVE™ from ADVANCED BIONICS® Corporation, which computes the center frequency of each band pass filter associated with the electrodes on the implanted electrode array based on the inputted implant fitting slope. In this manner, the fitting routine utilizing a harmonics-based tuner provides a correct mapping so that a sound perceived by the patient fitted with a cochlear stimulation system would sound like the same sound perceived by a normal hearing listener.

The disclosed fitting routine is notable because determination of the implant fitting slope of the implant fitting line does not require special musical training. A subject can quickly ascertain whether a sound presentation sounds like a single note. Not only is the disclosed fitting routine accurate, but the routine can be completed relatively quickly in a clinical setting because such sound presentations can be quickly implemented with appropriate programmable software. Because the disclosed fitting routine is based on the subject determining whether a sound presentation is a single note or a chord, the disclosed fitting routine is suited for those subjects that were pre-lingual at the onset of deafness, as wells those subjects that have had previous auditory experience.

FIG. 7 depicts an example of a menu interface to a computer software program that may be used to implement the steps described in FIG. 6. The menu interface at section 806 provides directions to the patient on how to use the computer software program. As can be seen, the patient is notified that one of the number keys 0 to 9 presents a sound comprised of one note and the remaining number keys present sounds containing two notes played at the same time. The patient is directed to press the "RETURN" key after each number key selection. If the patient believes a sound presentation consists of a single note, the patient is directed to press the letter key "q".

At section 810, a log of the patient's actions may be displayed. Here, the patient initially selected the number key "1" and then pressed return (as noted by label 814). The predetermined sound associated with the number key "1" was then presented to the patient. The patient then selected the number key "4" and then pressed return (as noted by label 816). Again, the predetermined sound associated with the number key "4" was then presented to the patient. The patient repeated this process of selecting a number key, pressing return and listening to sound associated with the selected number key until the patient eventually pressed the letter "q" (as noted by label 818) after having listened to the sound associated with the number key "2". To the patient, the perceived target sound, which was associated with the number key "2," sounded like a single note (as shown by label 824) with a actual (or delivered frequency) of 346.67 Hz (as shown by label 830). In this case, the target key was arbitrarily chosen to be the number key "7" (as shown by label 820) with an actual target frequency of 381.46 Hz (as shown by label 826).

The algorithms described above were then used to calculate the estimated offset 838 and the implant line slope 834. As can be seen, the offset 838 was calculated to be –1.66 semitones and the implant line slope 834 was calculated to be 7.51 mm/octave. Based on this information, the band pass filters associated with each electrode on the electrode array may then be adjusted resulting in a correct mapping of the electrodes to the perceived audio frequencies.

Figure 8A:
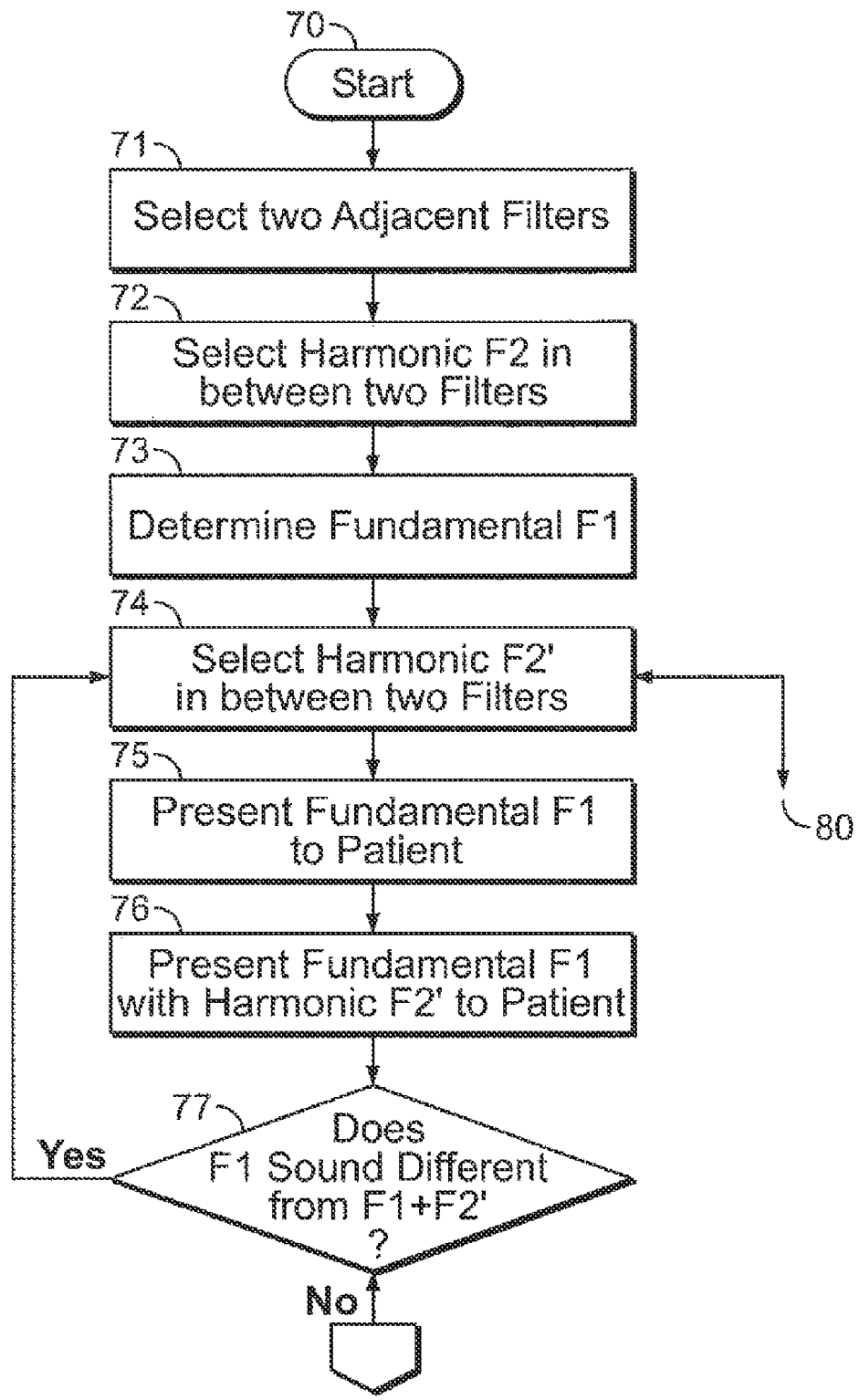
FIGS. 8A and 8B depict in flow chart form an alternative implementation of the fitting routing utilizing a harmonics-based tuner for aligning the band pass filters associated with each implanted electrode contact so as to permit the correct mapping of the implanted electrode array to the perceived audio frequencies.
Figure 8B:
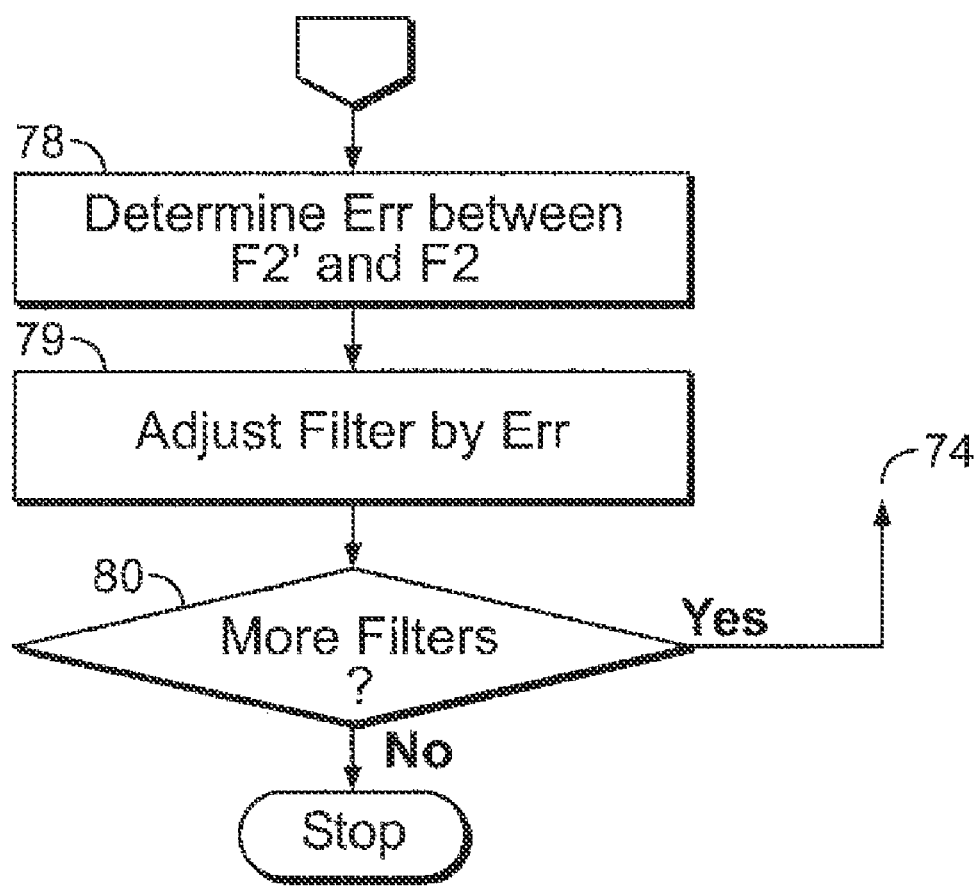

FIGS. 8A and 8B depict in flow chart form an alternative implementation of the fitting routing utilizing a harmonics-based tuner for aligning the band pass filters associated with each implanted electrode contact so as to permit the correct mapping of the implanted electrode array to the perceived audio frequencies. As noted above, to correctly map the implanted electrode array to the perceived audio frequencies, the patient's implant fitting slope typically must be determined. This alternative implementation calculates or adjusts the implant fitting slope between each electrode instead of calculating a uniform slope across the entire electrode array as done in the implementation associated with FIGS. 6 and 7, and may be described as follows. This alternative fitting routine provides a more accurate electrode-to-frequency mapping on a per electrode basis but generally takes more time to complete.

In general, this alternative implementation relies on the basic music theory that given a note is comprised of a fundamental F1 having an amplitude A1 and a series of harmonics, e.g., a second harmonic F2, a third harmonic F3, and a nth harmonic Fn, where F2 is 2*F1, F3 is 3*F1, and Fn is n*F1, with each harmonic having a smaller amplitude A2 . . . n, e.g., where A2=0.1*A1, then a sound including the fundamental F1 should sound the same to a normal hearing listener as a sound including the fundamental F1 and the small amplitude second harmonic F2. However, as mentioned above, due to the misalignment that typically results after an electrode array is surgically inserted, a patient fitted with a cochlear stimulation system typically will not reach the same conclusion as the normal hearing listener concerning the two same presentations. Nonetheless, a patient can still distinguish between sounds that are harmonically related and sounds that are not harmonically related. That is, if a patient is first presented with a sound including the fundamental F1 and then is next presented with a sound including the fundamental F1 and the small amplitude second harmonic F2, typically the patient will determine that the two presentations do not sound the same, primarily because the delivered (actual) second harmonic is not what is perceived by the patient. But if the second harmonic F2 was adjusted by a frequency offset to take into account the electrode array misalignment, then the patient should perceive the presentation of the fundamental F1 to be the same as the presentation of the fundamental F1 and the second harmonic adjusted by the offset, which may be referred to as the perceived second harmonic F2'.

This alternative implementation of the fitting routine may be described in detail as follows.

The starting point is step 70. The next step is shown in box 71, where two adjacent band pass filters, typically beginning with the second and third lowest frequency filter (e.g., filter 2 and filter 3), are selected as a starting point for the tuning process. Alternatively any two filters may be chosen, i.e., the two filters do not necessarily need be adjacent. For example, filter 1 and filter 3 may be selected and the following steps may then be used to determine the implant fitting slope of the electrodes associated with filter 1 and filter 3. Likewise, filter 3 and filter 8 may be selected and the following steps may then be used to determine the implant fitting slope of the electrodes associated with filter 3 and filter 8.

The next step, as shown by box 72, is to select at random an initial position of the small amplitude second harmonic F2 that is between the center frequencies of the two adjacent filters (or two arbitrarily chosen filters). Here, the second harmonic F2 was chosen to be 439 Hz. Next, as shown in box 73, the fundamental F1 of the second harmonic frequency F2 is determined by using the formula F1=F2/2. In this case, the fundamental F1 is 219.5 Hz. The next step, indicated by box 74, is to select at random an estimate of the perceived second harmonic frequency F2' that is offset from F2 and between the center frequencies of the two adjacent filters.

Next, as shown in box 75, the fundamental F1 is presented to the patient for a short period of time, e.g., 0.5 to 1 second(s), so that the patient has sufficient time to perceive the presented sound. Then, as shown in box 76, a sound including the fundamental F1 and the estimate of the perceived second harmonic F2' is presented to the patient for a similar period of time as the first sound presentation. Next, as shown in decision box 77, the patient compares the second sound presentation (i.e., F1 and F2') to the first sound presentation (i.e., F1) and determines whether the two presentations sound different (or the same). If the patient determines the two sound presentations sound different, the patient may change his estimate of the perceived second harmonic frequency F2', as represented by the return arrow back to box 74 from decision box 77. That is, another estimate of the perceived second harmonic frequency F2' may be interactively chosen and the two sound presentations once again can be played to the patient. In this iterative process, the frequencies of the estimated perceived second harmonic F2' should begin to converge to a value wherein further increments become smaller and do not provide appreciable improvement to the perceived similarity of the two presentations (F1 in one instance and F1 and F2' in another instance). The objective is to adjust the estimate of the perceived second harmonic F2' until the two presentations sound the same to the patient.

As shown in FIG. 8B, once no appreciable difference is detected between the two presentations, the difference (Err) between the estimate of the perceived second harmonic F2' and the actual second harmonic F2 is determined, as shown in box 78, by subtracting F2 from F2', i.e., Err=F2'−F2. Then, as shown in box 79, the center frequency of the higher frequency filter (filter 2) is adjusted by the difference (Err) in the direction of the estimate of the perceived second harmonic frequency F2' because it sounds to the patient like the actual second harmonic F2. The alignment for that particular filter (e.g., filter 2) is now complete. The implant fitting slope between the electrodes associated with the selected filters may then be easily determined, where the slope is mm/octave.

The iterative fitting process for aligning the filters may be analogized to the procedure for fitting eye glasses. The process for determining lens strength (diopters) is accomplished by presenting various lenses with various lens strength in a manner to "zero in" on the optimal lens prescription. The method requires starting with a lens of a particular prescription. Another lens strength is picked and then the better of the two is picked. Armed with this knowledge, a third lens may be selected and presented, and so forth, until a final, best lens is determined. The same iterative converging process may be used to determine the correct center frequency of the higher frequency filter of the two adjacent filters.

Then, as shown in decision box 80, if there are additional filters to align, the technique beginning at box 74 is applied to the filter just adjusted (e.g., filter 3) and the next higher frequency filter (e.g., filter 4). If there are not any more filters to align, the technique is completed, as shown by box 81.

Figure 9A:
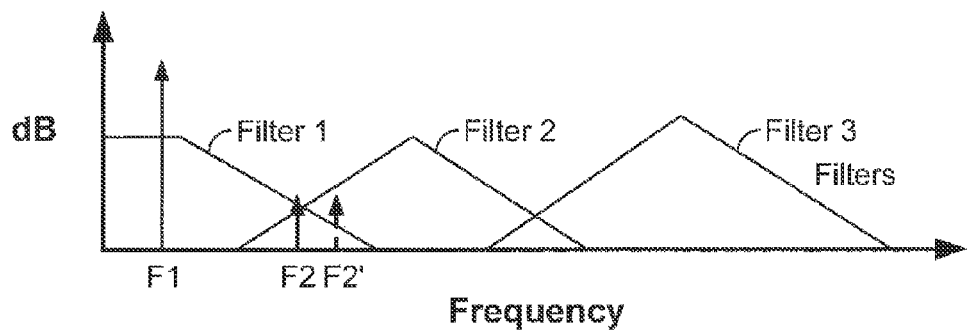
FIGS. 9A-9C illustrate in graphical form the alternative implementation of the fitting routine described in FIGS. 8A and 8B.
Figure 9B:
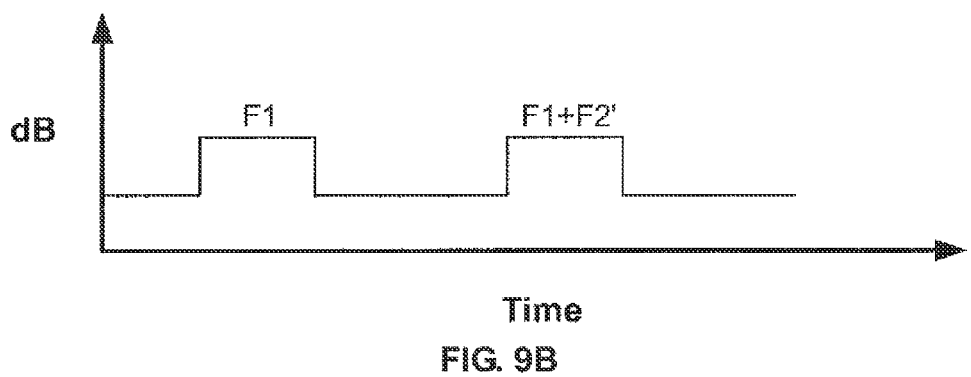
Figure 9C:
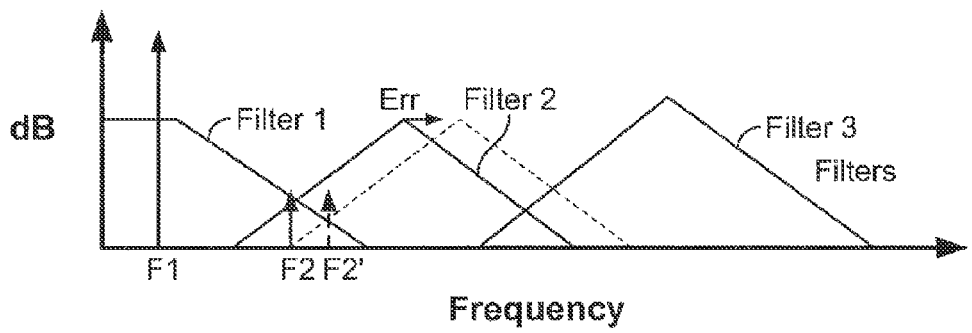

FIGS. 9A-9C illustrate in graphical form the alternative implementation of the fitting routine described in FIGS. 8A and 8B. As shown in FIG. 9A, a small amplitude second harmonic F2 is selected between filter 1 and filter 2. The fundamental F1 is shown to have a large amplitude compared to the amplitude of the second harmonic F2. A random location for the harmonic F2' is selected between filter 1 and filter 2. Here, the harmonic F2' is estimated to have a higher frequency than the second harmonic F2. Then, as shown in FIG. 9B, the patient is presented F1 for a short period of time (e.g., 1 to 2 seconds). After F1 is presented, then F1+F2' is presented to the patient for the same amount of time. If the two presentations sound different, the patient may change the estimate of the small amplitude harmonic F2'. If the two presentations sound the same, the difference between the harmonic F2' and the second harmonic F2 may be determined by the formula Err=F2'−F2. As shown in FIG. 9C, Err corresponds to the distance to move the center frequency of the higher frequency filter, i.e., filter 2, in the direction of F2'. This is because the harmonic F2' would sound to the user like the second harmonic F2. Once the filter 2 is adjusted, the same procedure may be used to adjust filter 3.

Figure 10A:
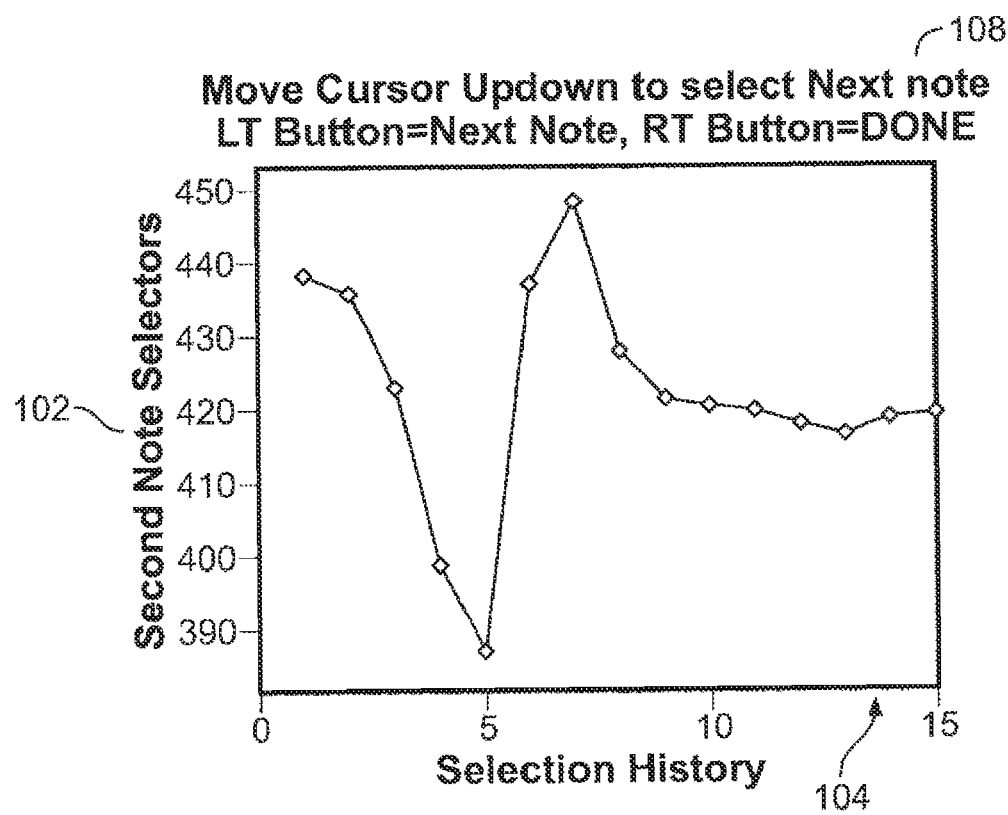
FIGS. 10A and 10B show an example of a menu interface to a computer software program that can be used to implement the steps presented in FIGS. 8A and 8B.
Figure 10B:
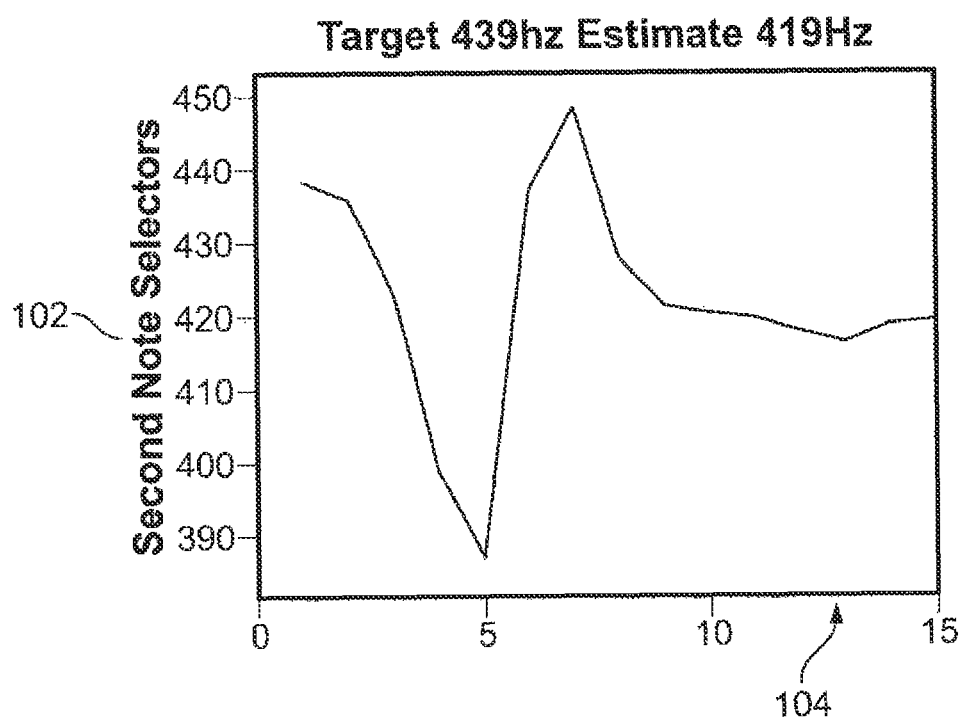

FIGS. 10A and 10B show an example of a user interface to a computer software program that can be used to implement the steps presented in FIGS. 8A and 8B. The user interface permits the patient to select a second fundamental from a list of a range of frequencies (Hz) on the Y axis 102. The X axis 104 represents the history for the fitting of a particular filter (e.g., filter 2). Thus, the patent can see which positions he has already tried (as shown in FIG. 10A). Once the patient finishes adjusting the second harmonic so that the two tones sound like a single note, the patient clicks on the right button of a mouse as directed by the user interface (as shown at label 108). The filter (e.g., filter 2) is then adjusted by the amount of the error between the frequency selected by the patient for the second harmonic and the actual position of the second harmonic. As shown in FIG. 10B, the target frequency was 439 Hz, the estimate frequency was 419 Hz, and the calculated implant line slope was 5.48 mm/octave. The patient may then proceed to adjust the next filter.

The computational aspects described here can be implemented in analog or digital electronic circuitry, or in computer hardware, firmware, software, or in combinations of them. Where appropriate, aspects of these systems and techniques can be implemented in a computer program product tangibly embodied in a machine-readable storage device for execution by a programmable processor; and method steps can be performed by a programmable processor executing a program of instructions to perform functions by operating on input data and generating output.

A number of implementations have been described. Other implementations may include different or additional features, for example, the filters associated with the electrode contacts need not be adjusted uniformly across the entire electrode array. Rather, the filters may be adjusted differently based on the implant fitting slope between regions of the electrode array. For example, in an electrode array having 16 electrode contacts, the implant fitting slope can be determined between electrodes 1-3 and the filters associated with electrodes 1-3 may be adjusted accordingly. Likewise, the implant fitting slope between electrodes 4-6 can be determined, and the filters associated with electrodes 4-6 may be adjusted accordingly, and so on in order to correctly map the electrode contacts.

Accordingly, other implementations are within the scope of the following claims.

What is claimed is:

1. A method of fitting a user's cochlear implant system using a computerized fitting system, wherein the cochlear implant system includes an electrode array having a plurality of electrodes implanted into a cochlea of a user, the method comprising:
   presenting from the computerized fitting system a plurality of sounds to the user through the electrode array, wherein each sound comprises a plurality of notes;
   receiving from the user at the computerized fitting system a selection of one of the plurality of sounds that most closely conforms to a single note; and
   determining at the computerized fitting system how to tune the cochlear implant system based on the received selection.

2. The method of claim 1, wherein presenting each of the sounds to the user through the electrode array is initiated by receiving from the user a unique computerized fitting system input corresponding to one of the sounds.

3. The method of claim 2, wherein each unique computerized fitting system input comprises a unique key of the computerized fitting system, each key being associated with one of the sounds.

4. The method of claim 1, wherein each electrode receives signals indicative of a band of frequencies in the plurality of sounds, and wherein determining how to tune the cochlear implant system comprises adjusting the band of frequencies that at least one of the electrodes receives.

5. The method of claim 4, wherein adjusting the band of frequencies that at least one electrode receives comprises adjusting a center frequency of at least one band pass filter in the cochlear implant system.

6. The method of claim 1, wherein a lowest of the notes in each of the plurality of sounds corresponds to a lowest center frequency of a band pass filter in the cochlear implant system.

7. The method of claim 1, wherein the implanted electrode array is placed in the scale tympani and the plurality of electrodes are spaced along the electrode array.

8. The method of claim 1, wherein determining how to tune the cochlear implant system comprises determining a slope of an implant fitting characteristic that defines a relationship between at least some of the electrodes in the electrode array and one or more audio frequencies.

9. The method of claim 1, further comprising programming a speech processor of the cochlear implant system with the determined tuning.

10. A method of fitting a user's cochlear implant system using a computerized fitting system, wherein the cochlear implant system includes an electrode array having a plurality of electrodes implanted into a cochlea of a user, the method comprising:
- presenting from the computerized fitting system a first tone to the user through the electrode array, wherein the first tone comprises a first frequency and a second frequency;
- presenting from the computerized fitting system a second tone to the user through the electrode array, wherein the second tone comprises the first frequency but not the second frequency;
- if the second tone does not sound like the first tone to the user, adjusting in the computerized fitting system the second frequency by an offset until the second tone sounds like the first tone to the user; and
- determining in the computerized fitting system how to tune the cochlear implant system using the offset.

11. The method of claim 10, wherein the second frequency is a harmonic of the first frequency.

12. The method of claim 10, wherein the adjusted second frequency is not a harmonic of the first frequency, but sounds like a harmonic of the first frequency to the user.

13. The method of claim 10, wherein each electrode receives signals indicative of a band of frequencies, and wherein determining how to tune the cochlear implant system using the offset comprises adjusting the band of frequencies that at least one of the electrodes receives.

14. The method of claim 13, wherein adjusting the band of frequencies that at least one electrode receives comprises adjusting a center frequency of at least one band pass filter in the cochlear implant system.

15. The method of claim 10, wherein the implanted electrode array is placed in the scale tympani and the plurality of electrodes are spaced along the electrode array.

16. The method of claim 10, wherein the first and second tones are presented at different times.

17. The method of claim 16, wherein the first and second tones are presented for the same amount of time.

18. The method of claim 10, wherein determining how to tune the cochlear implant system comprises determining a slope of an implant fitting characteristic that defines a relationship between at least some of the electrodes in the electrode array and audio frequencies.

19. The method of claim 10, further comprising programming a speech processor of the cochlear implant system with the determined tuning.

20. A method of fitting a user's cochlear implant system using a computerized fitting system, wherein the cochlear implant system includes an electrode array having a plurality of electrodes implanted into a cochlea of a user, the method comprising:
(a) presenting from the computerized fitting system a first tone to the user through the electrode array, wherein the first tone comprises a first frequency and a second frequency;
(b) presenting from the computerized fitting system a second tone to the user through the electrode array, wherein the second tone comprises the first frequency but not the second frequency;
(c) receiving from the user at the computerized fitting system an indication whether the second tone sounds like the first tone to the user;
(d) if the first tone and the second tone do not sound the same to the user, adjusting in the computerized fitting system the second frequency by an offset and repeating steps (a) through (c); and
(e) if the first tone and the second tone do sound the same to the user, determining in the computerized fitting system how to tune the cochlear implant system using the offset.

21. The method of claim 20, wherein the second frequency is a harmonic of the first frequency.

22. The method of claim 20, wherein the adjusted second frequency is not a harmonic of the first frequency, but sounds like a harmonic of the first frequency to the user.

23. The method of claim 20, wherein each electrode receives signals indicative of a band of frequencies, and wherein determining how to tune the cochlear implant system using the offset comprises adjusting the band of frequencies that at least one of the electrodes receives.

24. The method of claim 23, wherein adjusting the band of frequencies that at least one electrode receives comprises adjusting a center frequency of at least one band pass filter in the cochlear implant system.

25. The method of claim 20, wherein the first and second tones are presented at different times.

26. The method of claim 25, wherein the first and second tones are presented for the same amount of time.

27. The method of claim 20, wherein determining how to tune the cochlear implant system comprises determining a slope of an implant fitting characteristic that defines a relationship between at least some of the electrodes in the electrode array and audio frequencies.

28. The method of claim 20, further comprising programming a speech processor of the cochlear implant system with the determined tuning.

29. A method of fitting a user's cochlear implant system using a computerized fitting system, wherein the cochlear implant system includes an electrode array having a plurality of electrodes implanted into a cochlea of a user, wherein each electrode receives signals within a frequency band, the method comprising:
- presenting from the computerized fitting system a first tone to the user through the electrode array comprising a first frequency and a second frequency, wherein the first frequency is within a first frequency band and wherein the second frequency is within a second frequency band;
- adjusting in the computerized fitting system the second frequency in the first tone by a first offset until the first tone sounds like a single note to the user; and
- determining in the a computerized fitting system how to tune the second frequency band in the cochlear implant system using the first offset.

30. The method of claim 29, wherein the adjusted second frequency sounds like a harmonic of the first frequency to the user.

31. The method of claim 30, wherein determining how to tune the second frequency band comprises determining how to tune a center frequency of the second frequency band.

32. The method of claim 29, wherein the first and second frequency bands are adjacent.

33. The method of claim 29, wherein the first frequency band is received at a first electrode, and wherein the second frequency band is received at a second electrode.

34. The method of claim 29, further comprising programming a band pass filter in a speech processor of the cochlear implant system with the determined tuning for the second frequency band.

35. The method of claim 29, subsequently comprising:

presenting from the computerized fitting system a second tone to the user through the electrode array comprising a third frequency and a fourth frequency, wherein the third frequency is within the second tuned frequency band and wherein the fourth frequency is within a third frequency band;

adjusting in the computerized fitting system the fourth frequency in the second tone by a second offset until the second tone sounds like a single note; and determining in the computerized fitting system how to tune the third frequency band in the cochlear implant system using the second offset.

36. The method of claim 35, wherein the adjusted fourth frequency sounds like a harmonic of the third frequency to the user.

37. The method of claim 36, wherein determining how to tune the third frequency band comprises determining how to tune a center frequency of the third frequency band.

38. The method of claim 35, wherein the second and third frequency bands are adjacent.

39. The method of claim 35, wherein the second tuned frequency band is received at a second electrode, and wherein the third frequency band is received at a third electrode.

40. The method of claim 35, further comprising programming band pass filters in a speech processor of the cochlear implant system with the determined tunings for the second and third frequency bands.

* * * * *